(12) United States Patent
Ogawa

(10) Patent No.: US 9,157,728 B2
(45) Date of Patent: Oct. 13, 2015

(54) ENDOSCOPE APPARATUS AND METHOD

(75) Inventor: Kiyotomi Ogawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 912 days.

(21) Appl. No.: 12/839,560

(22) Filed: Jul. 20, 2010

(65) Prior Publication Data

US 2011/0021874 A1 Jan. 27, 2011

(30) Foreign Application Priority Data

Jul. 24, 2009 (JP) ................ P2009-173536

(51) Int. Cl.
| | | |
|---|---|---|
| *A61B 1/00* | (2006.01) | |
| *A61B 1/04* | (2006.01) | |
| *A61B 1/06* | (2006.01) | |
| *G01B 11/02* | (2006.01) | |
| *A61B 5/00* | (2006.01) | |
| *G02B 23/24* | (2006.01) | |
| *A61B 1/05* | (2006.01) | |
| *A61B 5/107* | (2006.01) | |

(52) U.S. Cl.
CPC ............ *G01B 11/026* (2013.01); *A61B 5/6885* (2013.01); *G02B 23/2484* (2013.01); *A61B 1/05* (2013.01); *A61B 5/1076* (2013.01)

(58) Field of Classification Search
CPC .................. A61B 1/00009; A61B 2019/5268; A61B 19/56
USPC ................. 600/117, 118, 160, 166, 178, 180; 348/69
See application file for complete search history.

(56) References Cited

U.S. PATENT DOCUMENTS

| | | | | | |
|---|---|---|---|---|---|
| 5,573,492 | A | * | 11/1996 | Dianna et al. ................. | 600/117 |
| 5,669,871 | A | * | 9/1997 | Sakiyama ..................... | 600/117 |
| 5,993,378 | A | * | 11/1999 | Lemelson ..................... | 600/109 |
| 6,009,189 | A | * | 12/1999 | Schaack ........................ | 382/154 |
| 6,161,035 | A | * | 12/2000 | Furusawa ..................... | 600/476 |
| 6,714,841 | B1 | * | 3/2004 | Wright et al. ................. | 700/259 |
| 6,945,930 | B2 | * | 9/2005 | Yokota .......................... | 600/118 |
| 7,324,673 | B1 | * | 1/2008 | Yamanaka et al. ............ | 382/128 |
| 2004/0054256 | A1 | * | 3/2004 | Ogawa .......................... | 600/118 |
| 2005/0023356 | A1 | * | 2/2005 | Wiklof et al. ............ | 235/462.42 |
| 2006/0178561 | A1 | * | 8/2006 | Nakano et al. ................ | 600/117 |
| 2006/0268257 | A1 | * | 11/2006 | Ogawa ......................... | 356/3.13 |
| 2008/0198223 | A1 | * | 8/2008 | Iriyama ......................... | 348/65 |
| 2009/0149713 | A1 | | 6/2009 | Niida | |

FOREIGN PATENT DOCUMENTS

| | | |
|---|---|---|
| JP | 01-207032 A | 8/1989 |
| JP | 04-332523 A | 11/1992 |

(Continued)

OTHER PUBLICATIONS

Japanese Office Action dated Feb. 5, 2013 (and English translation thereof) in counterpart Japanese Application No. 2009-173536.

*Primary Examiner* — Anhtuan T Nguyen
*Assistant Examiner* — William Chou
(74) *Attorney, Agent, or Firm* — Holtz, Holtz, Goodman & Chick PC

(57) ABSTRACT

An endoscope apparatus includes: an imaging unit which takes an image of an object; a display which displays the image and a cursor; an illumination unit which illuminates the object; a pointing device which is for placing the cursor; and a control unit which continuously monitors a cursor position placed by the pointing device, and continuously controls the illumination unit in accordance with a luminance of a partial region of the image corresponding to the cursor position so as to modulate a luminance condition of the image.

21 Claims, 12 Drawing Sheets

(56) References Cited

FOREIGN PATENT DOCUMENTS

| | | |
|---|---|---|
| JP | 06-339454 A | 12/1994 |
| JP | 08-114755 A | 5/1996 |
| JP | 11-225952 A | 8/1999 |
| JP | 2002-209841 A | 7/2002 |
| JP | 2003-107567 A | 4/2003 |
| JP | 2006-136706 A | 6/2006 |
| JP | 2006-325741 A | 12/2006 |
| JP | 2008-048905 A | 3/2008 |

* cited by examiner

ENDOSCOPE APPARATUS AND METHOD

BACKGROUND OF THE INVENTION

1. Field of the Invention

The present invention relates to an endoscope apparatus which has a function of modulating a luminance condition of an image of an object, and a method thereof.

Priority is claimed on Japanese Patent Application No. 2009-173536, filed Jul. 24, 2009, the content of which is incorporated herein by reference.

2. Description of the Related Art

An endoscope apparatus is used to observe or inspect internal damage, corrosion, and the like, of a boiler, a turbine, an engine, a pipe, and the like. In addition, there is known a measurement endoscope apparatus having a function of measuring a length, an area, and the like, using the principle of triangulation on the basis of a measurement point designated on an image imaged by an endoscope. Japanese Unexamined Patent Application, First Publication No. 2006-136706 and Japanese Unexamined Patent Application, First Publication No. 2006-325741 disclose measurement endoscope apparatuses capable of informing a user whether or not a distal end of an endoscope is close to an object (observation object) at a distance suitable for measurement in such a manner that a distance (object distance) from the distal end of the endoscope to the object is displayed in real time.

SUMMARY OF THE INVENTION

According to an aspect of the present invention, there is provided an endoscope apparatus including: an imaging unit which takes an image of an object; a display which displays the image and a cursor; an illumination unit which illuminates the object; a pointing device which is for placing the cursor; and a control unit which continuously monitors a cursor position placed by the pointing device, and continuously controls the illumination unit in accordance with a luminance of a partial region of the image corresponding to the cursor position so as to modulate a luminance condition of the image.

DETAILED DESCRIPTION OF THE INVENTION

Figure 1:
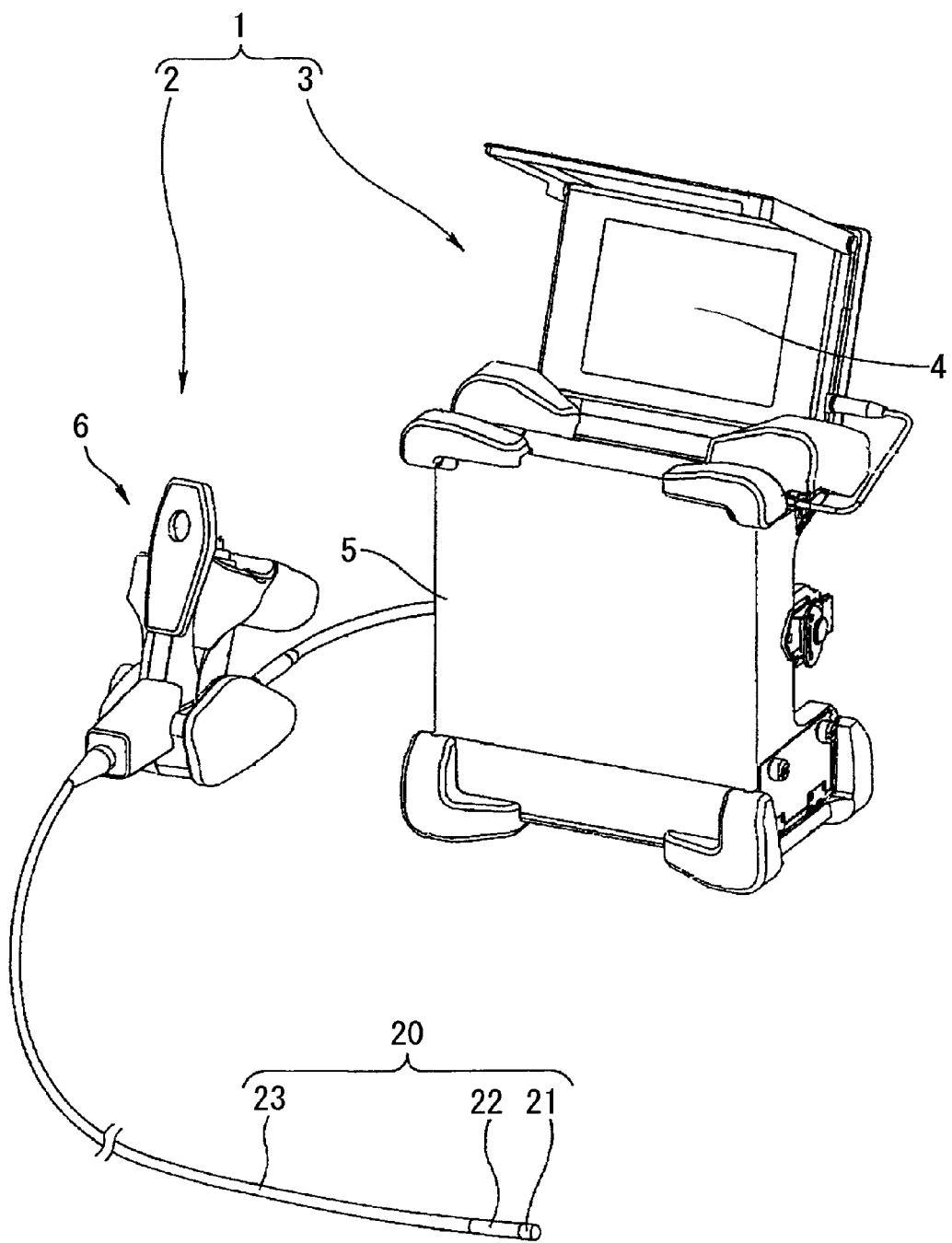
FIG. 1 is a perspective view showing an entire configuration of an endoscope apparatus according to an embodiment of the present invention.

Hereinafter, an embodiment of the present invention will be described with reference to the accompanying drawings. FIG. 1 shows an entire configuration of an endoscope apparatus according to an embodiment of the present invention. As shown in FIG. 1, an endoscope apparatus 1 includes an endoscope 2 and a main body 3 which is connected to the endoscope 2. The endoscope 2 includes a thin and long insertion portion 20 and an operation portion 6 which is used for performing an operation of controlling the apparatus. The main body 3 includes a monitor (liquid crystal monitor) 4 which is a display device displaying an object image imaged by the endoscope 2, information (for example, an operation menu) relating to an operation, and the like, and a casing 5 which includes a control unit 10 (refer to FIG. 2).

The insertion portion 20 includes a rigid distal end portion 21, a bent portion 22 which is able to be bent, for example, in the vertical and horizontal directions, and a flexible tube portion 23 which has flexibility, where the distal end portion 21, the bent portion 22, and the tube portion 23 are sequentially arranged. Various optical adapters, such as a stereo optical adapter having two observation fields of view or an optical adapter having one observation field of view, can be attached to the distal end portion 21 in a freely detachably manner.

Figure 2:
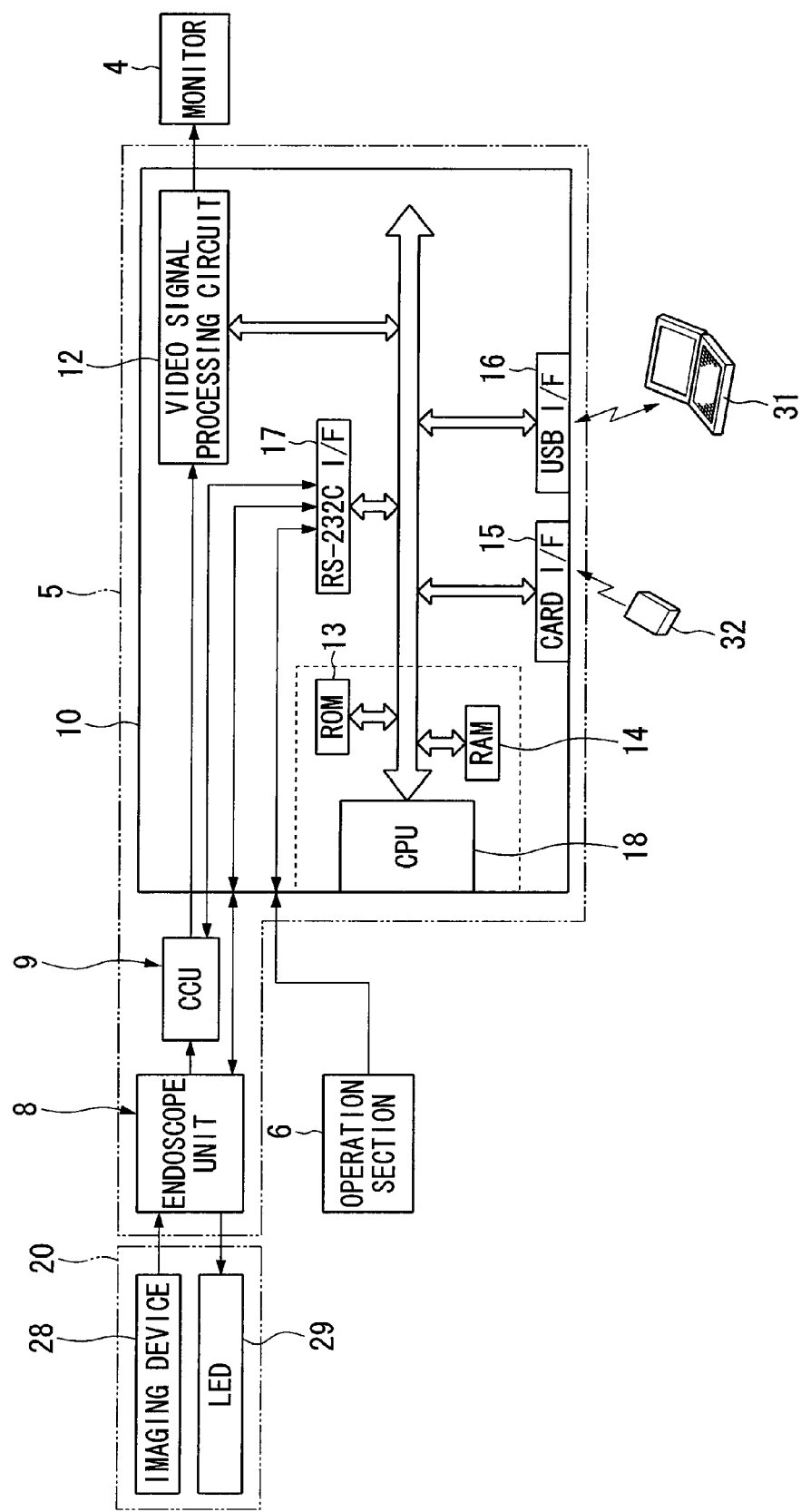
FIG. 2 is a block diagram showing an internal configuration of the endoscope apparatus according to the embodiment of the present invention.

As shown in FIG. 2, the casing 5 includes an endoscope unit 8, a CCU (camera control unit) 9, and the control unit 10. The proximal end portion of the insertion portion 20 is connected to the endoscope unit 8. The endoscope unit 8 includes a light source driving mechanism which drives a light source (LED) 29 built in the distal end portion 21 and a bending mechanism which bends the bent portion 22 constituting the insertion portion 20.

An imaging device 28 and the LED 29 are built in the distal end portion 21. The imaging device 28 performs a photoelectric conversion of an object image captured through the optical adapter to create an image signal. The image signal output from the imaging device 28 is input to the CCU 9. The image signal is converted into a video signal (image data) such as an NTSC signal by the CCU 9, and the result is supplied to the control unit 10. The LED 29 generates illumination light for illuminating the object.

The control unit 10 includes a video signal processing circuit 12 to which the video signal is input, a ROM 13, a RAM 14, a card I/F (card interface) 15, a USB I/F (USB interface) 16, an RS-232C I/F (RS-232C interface) 17, and a CPU 18 which executes various functions on the basis of the program and controls the endoscope apparatus 1.

The RS-232C I/F 17 is connected to the CCU 9, the endoscope unit 8, and the operation portion 6 which performs control and operation instructions of the CCU 9, the endoscope unit 8, and the like. When a user operates the operation portion 6, a communication required for controlling the CCU 9 and the endoscope unit 8 is performed in accordance with the type of the operation.

The USB I/F 16 is an interface which electrically connects the control unit 10 and a personal computer 31 to each other. When the control unit 10 and the personal computer 31 are connected to each other through the USB I/F 16, it is possible to perform an instruction for displaying an endoscope image and various instructions such as an image process during measurement, at the personal computer 31 side. In addition, it is possible to input and output information, data for a control required for various processes, and the like between the control unit 10 and the personal computer 31.

In addition, a memory card 32 is freely attached to or detached from the card I/F 15. When the memory card 32 is attached to the I/F 15, it is possible to take data, such as control-processing information or image data stored in the memory card 32 into the control unit 3, or to store data, such as the control-processing information and the image data, in the memory card 32, in accordance with the control of the CPU 18.

The video signal processing circuit 12 performs a process of combining the video signal from the CCU 9 with a graphic image signal based on the operation menu created by the control of the CPU 18 in order to display a composite image obtained by combining the endoscope image based on the video signal supplied from the CCU 9 with the graphic image of the operation menu, and a process required for performing display the composite image on a screen of the monitor 4, and supplies a display signal to the monitor 4. In addition, the video signal processing circuit 12 may perform a process for independently displaying only the endoscope image or only the image of the operation menu. Accordingly, the endoscope image, the operation menu, or the composite image of the endoscope image and the operation menu, is displayed on the screen of the monitor 4.

The CPU 18 executes a program that is stored in the ROM 13, whereby various circuits and the like are controlled so as to perform processes depending on the purpose, and controls the endoscope apparatus 1. The RAM 14 is used as a work area for temporary storage of data by the CPU 18.

Figure 3:
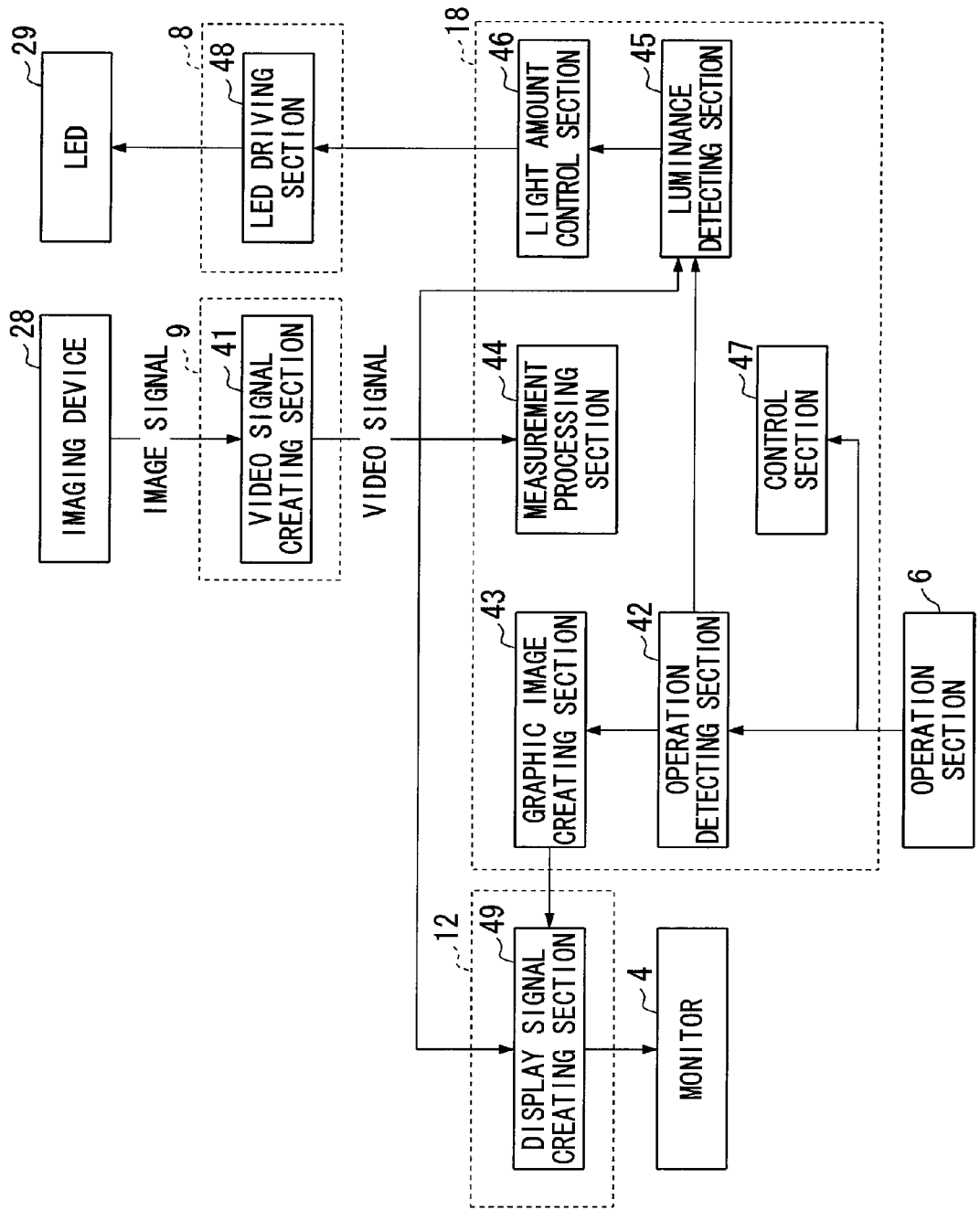
FIG. 3 is a block diagram showing a functional configuration of the endoscope apparatus according to the embodiment of the present invention.

FIG. 3 shows a functional configuration of a part of the endoscope apparatus 1. A video signal creating section 41 corresponds to the function of the CCU 9. The video signal creating section 41 creates a video signal on the basis of the image signal output from the imaging device 28.

An operation detecting section 42, a graphic image creating section 43, a measurement processing section 44, a luminance detecting section 45, a light amount control section 46, and a control section 47 correspond to the functions of the CPU 18. The operation detecting section 42 detects an operation of the operation portion 6 operated by the user, and sets a display position of a sight displayed on the screen of the monitor 4 in accordance with the type of the operation. The sight includes a spot for designating a position of calculating an object distance and a cursor for designating a position of setting a measurement point. The object distance is a distance from the distal end portion 21 to the object and, for example, a distance from the imaging device 28 or an observation optical system to the object. The user is able to move the sight on the screen by operating a pointing device (direction lever) provided in the operation portion 6. The examples of the pointing device include a mouse, a track ball, a track pad, and a touch panel.

The graphic image creating section 43 creates a graphic image signal corresponding to the sight or the operation menu displayed on the screen of the monitor 4. As described above, the display position of the sight on the screen is set by the operation detecting section 42. The measurement processing section 44 performs an object distance calculating process and a measurement process on the basis of the video signal created by the video signal creating section 41. The object distance calculating process is a process for calculating the object distance. The measurement process is a process for calculating dimensions of the object, an area or a length for example, designated at the measurement points set on the endoscope image. In the description of the embodiment, the object distance calculating process and the measurement process are divided from each other, but the object distance calculating process may be included in the measurement process in the broad meaning.

The luminance detecting section 45 detects a luminance of a partial region on the image based on the video signal created by the video signal creating section 41, the partial region being set based on a display position of the spot set by the operation detecting section 42. The light amount control section 46 outputs a control signal for controlling (modulating) the light amount of the LED 29 on the basis of the luminance detected by the luminance detecting section 45. The light amount control section 46 may control a shutter speed of the imaging device 28 on the basis of the luminance detected by the luminance detecting section 45. In other words, the light amount control section 46 controls the light amount which the imaging device 28 receives. Furthermore, gain characteristics of the image acquired by the imaging device 28 may be controlled. The control section 47 controls the process allocation to the operation detecting section 42, the graphic image creating section 43, the measurement processing section 44, the luminance detecting section 45, and the light amount control section 46, and controls the entire operation of the endoscope apparatus 1.

The LED driving section 48 corresponds to the function of the endoscope unit 8. The LED driving section 48 outputs a driving signal for driving the LED 29 on the basis of the control signal output from the light amount control section 46. The LED 29 emits light on the basis of the driving signal output from the LED driving section 48. The display signal creating section 49 corresponds to the function of the video signal processing circuit 12. The display signal creating section 49 creates a display signal by combining the video signal created by the video signal creating section 41 with the graphic image signal created by the graphic image creating section 43. The monitor 4 displays an image on the basis of the display signal created by the display signal creating section 49.

Figure 4:
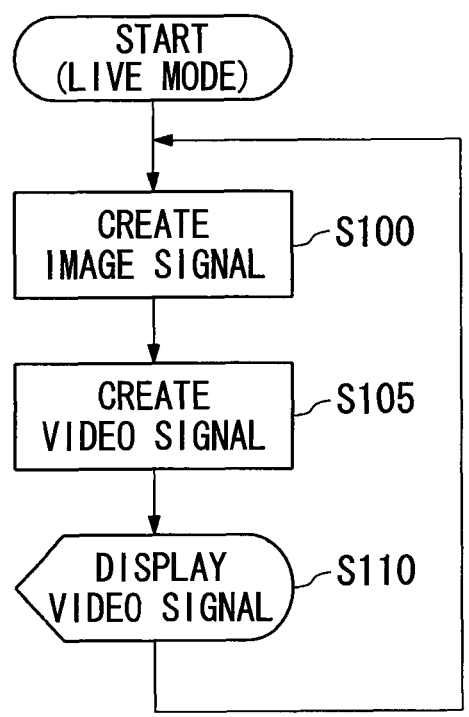
FIG. 4 is a flowchart showing a sequence of an operation of the endoscope apparatus according to the embodiment of the present invention.

Next, an operation of the endoscope apparatus 1 according to the embodiment will be described. When the endoscope apparatus 1 is powered on, the endoscope apparatus 1 is in a live mode in which an imaging operation and an image displaying operation are repeatedly performed. As shown in FIG. 4, in the live mode, the imaging device 28 images the object, and creates an image signal (Step S100).

The video signal creating section 41 converts the image signal into a video signal (Step S105).

The display signal creating section 49 creates a display signal by combining the video signal with a graphic image signal from the graphic image creating section 43, and outputs the display signal to the monitor 4. The monitor 4 displays an image on the basis of the display signal (Step S110). Subsequently, the process returns to Step S100. During Step S100 to Step S110, the control section 47 constantly monitors a signal from the operation portion 6, and determines whether or not the user performs an operation of activating an object distance calculating function. The operation of activating the object distance calculating function is an operation of inputting an instruction of calculating the object distance. In the case where the user performs the operation of activating the object distance calculating function, the endoscope apparatus 1 is in a start state of the object distance calculation.

Figure 5:
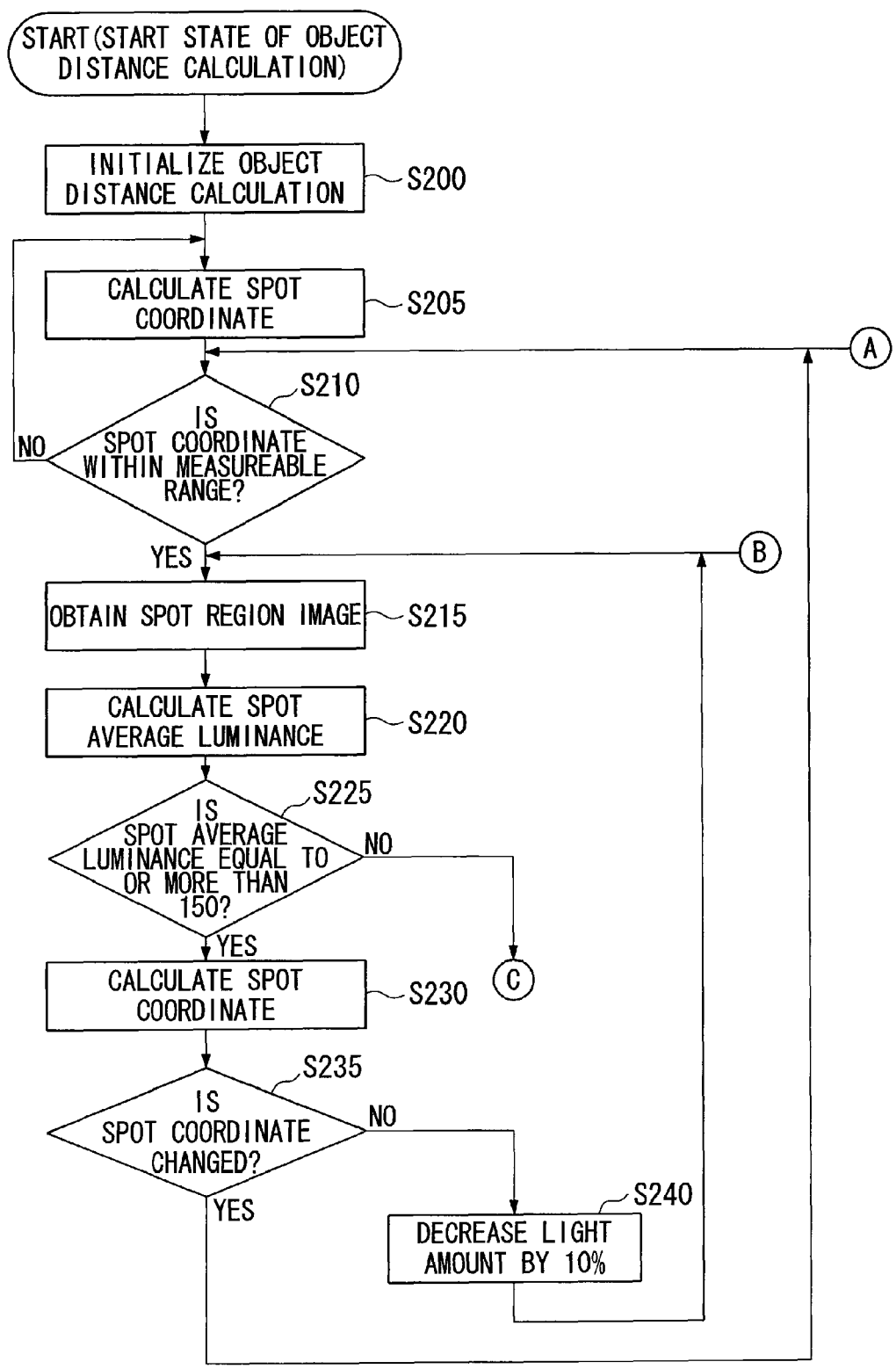
FIG. 5 is a flowchart showing a sequence of an operation of the endoscope apparatus according to the embodiment of the present invention.
Figure 6:
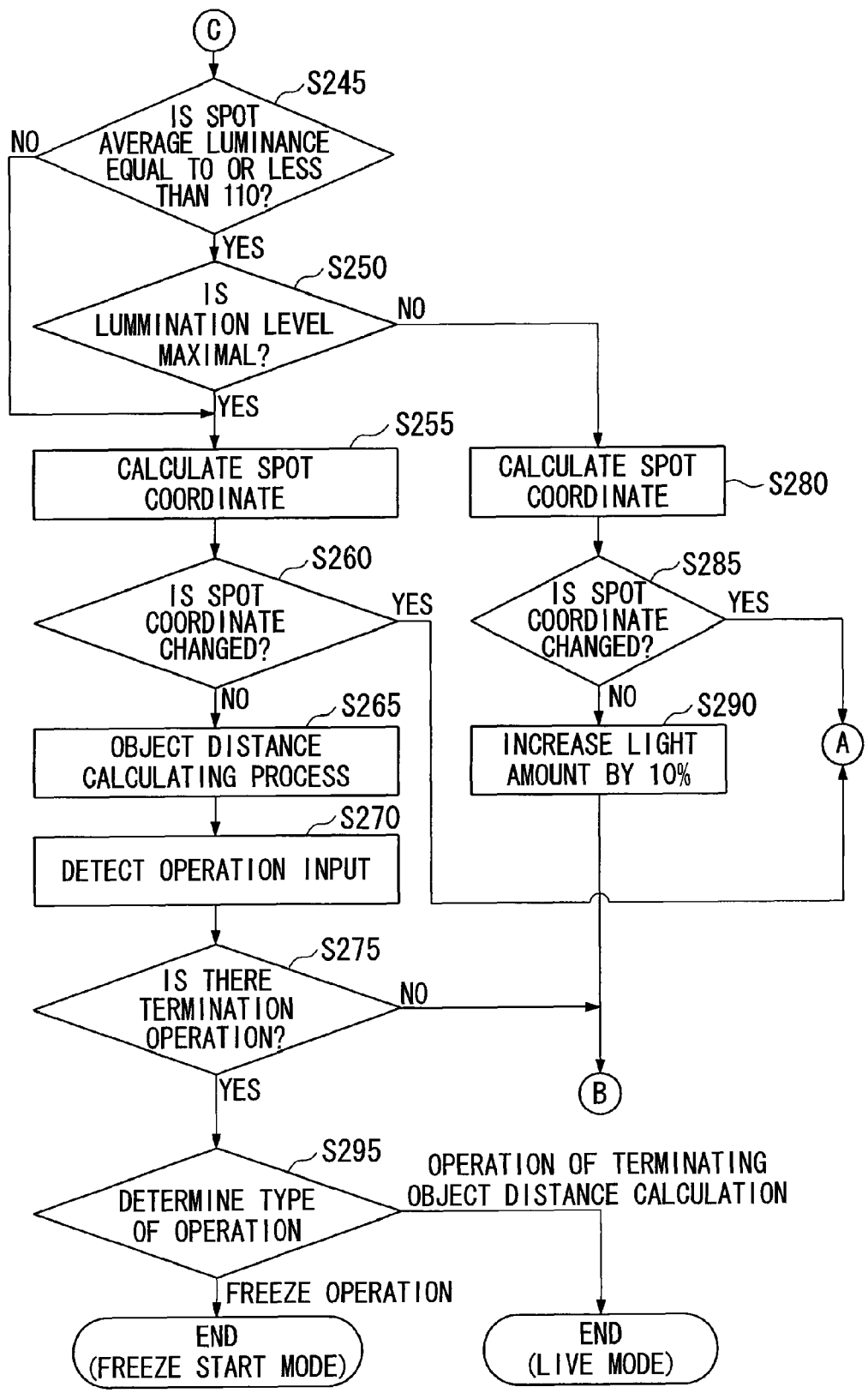
FIG. 6 is a flowchart showing a sequence of an operation of the endoscope apparatus according to the embodiment of the present invention.

In the start state of the object distance calculation, as shown in FIGS. 5 and 6, the light amount of the LED 29 is modulated so that the luminance of a partial region on the image based on the video signal is within a predetermined range, and the object distance is calculated. In addition, in the start state of the object distance calculation, the processes in Step S100 to Step S110 of FIG. 4 are continuously performed at the same time. In the start state of the object distance calculation, first, a region for various variables is ensured in the RAM 14, and the variables are initialized. At this time, as a region for storing a display coordinate (hereinafter, referred to as a spot coordinate) of the spot displayed on the screen of the monitor 4, a region (hereinafter, referred to as a first region) for storing a current spot coordinate and a region (hereinafter, referred to as a second region) for storing a previous spot coordinate are allocated (Step S200).

Subsequently, the operation detecting section 42 calculates the spot coordinate in accordance with the operation of the operation portion 6 operated by the user, and stores the spot coordinate in the RAM 14. At this time, the spot coordinate which has been stored in the first region is stored in the second region, and the newly calculated spot coordinate is stored in the first region (Step S205).

Subsequently, the control section 47 reads the spot coordinate from the first region of the RAM 14, and determines whether or not the spot coordinate is within a measurable range (Step S210). In the case where the spot coordinate is not within the measurable range, the process returns to Step S205. In addition, in the case where the spot coordinate is within the measurable range, the luminance detecting section 45 receives a video signal of a spot region which is a region of, for example, 21 by 21 pixels centered on the spot coordinate (Step S215). Subsequently, the luminance detecting section 45 calculates an average luminance (hereinafter, referred to as a spot average luminance) of the spot region on the basis of the video signal received in Step S215 (Step S220).

Subsequently, the control section 47 determines whether or not the spot average luminance is equal to or more than 150 (Step S225). In the case where the spot average luminance is less than 150, the process advances to Step S245 of FIG. 6. In addition, in the case where the spot average luminance is equal to or more than 150, the operation detecting section 42 calculates the spot coordinate in accordance with the operation of the operation portion 6 operated by the user, and stores the spot coordinate in the RAM 14. At this time, the spot coordinate which has been stored in the first region is stored in the second region, and the newly calculated spot coordinate is stored in the first region (Step S230).

Subsequently, the control section 47 reads the spot coordinates from the first and second regions of the RAM 14, and determines whether or not both are different, that is, the spot coordinate is changed (Step S235). In the case where the spot coordinate is changed, the process returns to Step S210. In addition, in the case where the spot coordinate is not changed, the light amount control section 46 outputs a control signal for reducing the light amount of the LED 29 by 10% (Step S240). The LED driving section 48 outputs the driving signal for driving the LED 29 on the basis of the control signal and the LED 29 emits light on the basis of the driving signal. Subsequently, the process returns to Step S215.

In the case where the process advances to Step S245 of FIG. 6, the control section 47 determines whether or not the spot average luminance is equal to or less than 110 (Step S245). In the case where the spot average luminance exceeds 110, the process advances to Step S255. In addition, in the case where the spot average luminance is equal to or less than 110, the control section 47 determines whether or not the light amount of the LED 29 set in the light amount control section 46 is maximal (Step S250). In the case where the light amount is maximal, the process advances to Step S255. In the case where the light amount is not maximal, the process advances to Step S280.

In the case where the process advances to Step S255, the operation detecting section 42 calculates the spot coordinate in accordance with the operation of the operation portion 6 operated by the user, and stores the spot coordinate in the RAM 14. At this time, the spot coordinate which has been stored in the first region is stored in the second region, and the newly calculated spot coordinate is stored in the first region (Step S255). Subsequently, the control section 47 reads the spot coordinates from the first and second regions of the RAM 14, and determines whether or not both are different, that is, the spot coordinate is changed (Step S260). In the case where the spot coordinate is changed, the process returns to Step S210. In addition, in the case where the spot coordinate is not changed, the process advances to Step S265.

In the case where the process advances to Step S280, as in Step S255, the spot coordinate is calculated (Step S280). Subsequently, as in Step S260, it is determined whether or not the spot coordinate is changed (Step S285). In the case where the spot coordinate is changed, the process returns to Step S210. In addition, in the case where the spot coordinate is not changed, the light amount control section 46 outputs a control signal for increasing the light amount of the LED 29 by 10% (Step S290). The LED driving section 48 outputs the driving signal for driving the LED 29 on the basis of the control signal and the LED 29 emits light on the basis of the driving signal. Subsequently, the process returns to Step S215.

Figure 11:
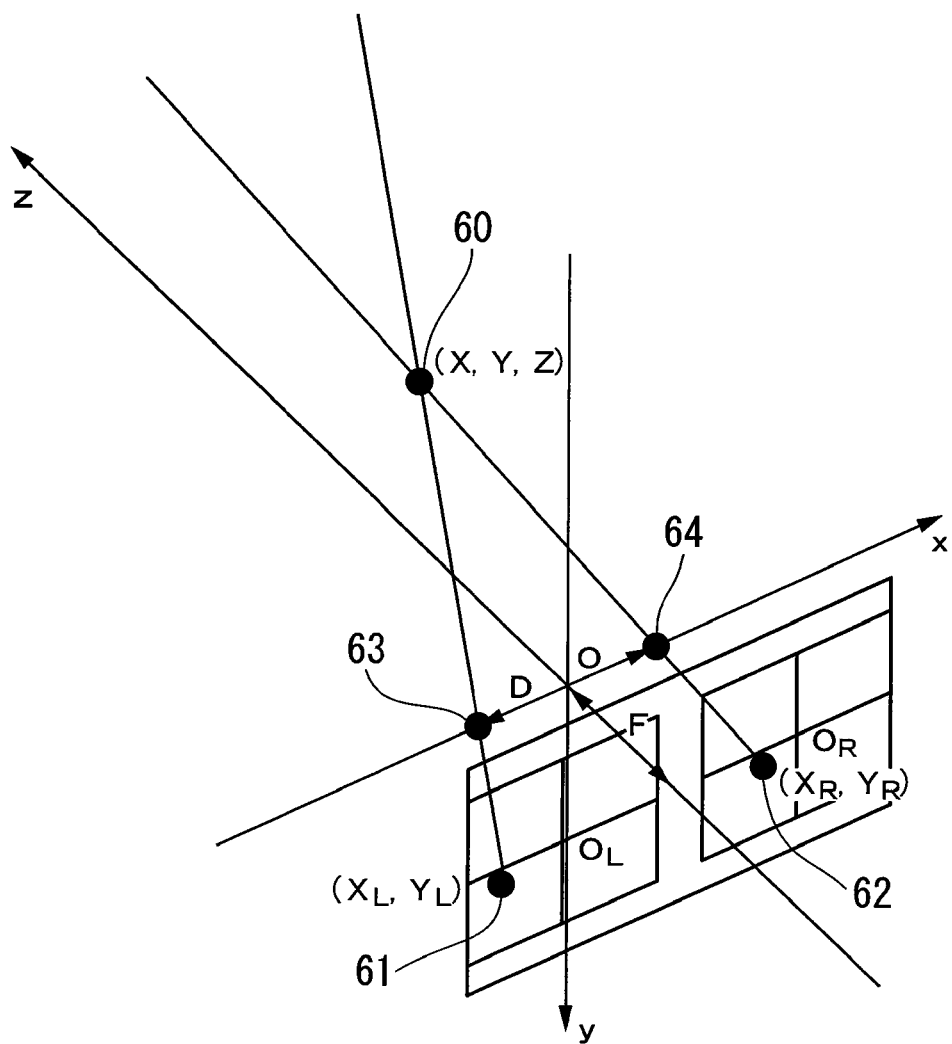
FIG. 11 is a reference diagram illustrating a method of obtaining a three-dimensional coordinate of a measurement point by using a stereo measurement.

In the case where the process advances to Step S265, the measurement processing section 44 performs the object distance calculating process of calculating the object distance on the basis of the video signal (Step S265). In the object distance calculating process, a three-dimensional coordinate of a measurement point located at the spot coordinate is calculated through the stereo measurement using the principle of triangulation, and the object distance is calculated. Hereinafter, by referring to FIG. 11, a method of obtaining the three-dimensional coordinate of the measurement point using the stereo measurement will be described. For images that are imaged by the left and right optical systems, a three-dimensional coordinate (X, Y, Z) of a measurement point 60 is calculated by a method of triangulation using the following equations (1) to (3). Here, the coordinates of the measurement points 61 and 62 on the left and right images subjected to distortion correction are respectively set to $(X_L, Y_L)$ and $(X_R, Y_R)$, the distance between the left and right optical centers 63 and 64 is set to D, the focal length is set to F, and $t=D/(X_L-X_R)$.

$$X = t \times X_R + D/2 \tag{1}$$

$$Y = t \times Y_R \tag{2}$$

$$Z = t \times F \tag{3}$$

As described above, when the coordinates of the measurement points 61 and 62 on the original images are determined, the three-dimensional coordinate of the measurement point 60 is calculated by using the parameters D and F. When the three-dimensional coordinates of several points are calculated, it is possible to perform various measurements such as: a distance between two points; a distance, a depth, and an area between a line connecting two points and one point; and a surface shape. In addition, it is possible to calculate a distance (object distance) from the left optical center 63 or the right optical center 64 to the object. In order to perform the above-described stereo measurement, it is necessary to prepare optical data representing a characteristic of an optical system including the distal end portion 21 of the endoscope and the stereo optical adapter. Note that since the details of the optical data are described in, for example, Japanese Unexamined Patent Application, First Publication No. 2004-49638, an explanation thereof will be omitted here.

When the object distance calculating process terminates, the control section 47 detects the signal from the operation portion 6 (Step S270), and determines whether or not the user performs a termination operation (Step S275). The termination operation is a freeze operation or an operation of terminating the object distance calculation. The freeze operation is an operation of inputting an instruction of displaying a still image. In the case where the user does not perform the termination operation, the process returns to Step S215. In addition, in the case where the user performs the termination operation, the control section 47 determines whether the end operation is the freeze operation or the operation of terminating the object distance calculation (Step S295). In the case where the termination operation is the freeze operation, the endoscope apparatus 1 is in a freeze mode. In addition, in the case where the termination operation is the operation of terminating the object distance calculation, the endoscope apparatus 1 is in the live mode.

According to the processes shown in FIGS. 5 and 6, the light amount of the LED 29 is modulated so that the luminance of the spot region is suitable for the measurement.

In addition, the same processes as those in Step S100 to S110 of FIG. 4 are repeatedly performed together with the processes shown in FIGS. 5 and 6. Accordingly, the screen of the monitor 4 is periodically updated, and the display position of the spot is changed in accordance with the operation of the operation portion 6 operated by the user.

In the processes shown in FIGS. 5 and 6, the spot coordinate is continuously monitored and the light amount of the LED 29 is continuously modulated during a period in time from the input of the operation of activating an object distance calculating function until the input of the termination operation.

Figure 9A:
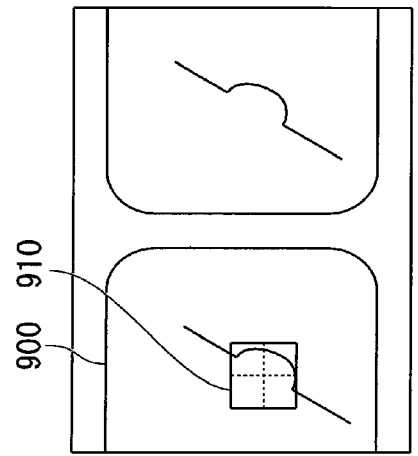
FIGS. 9A to 9F are reference diagrams showing screens according to the embodiment of the present invention.
Figure 9B:
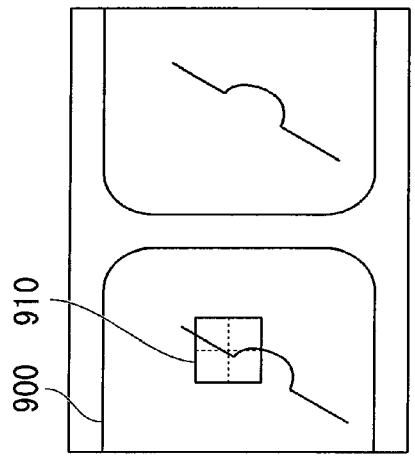
Figure 9C:
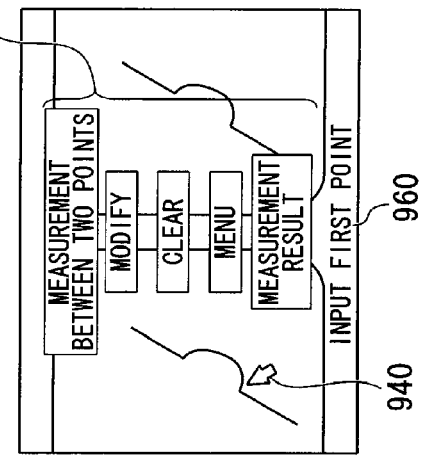

FIG. 9A shows a screen of the monitor 4 in the live mode. A pair of left and right images 900 and 901, which are imaged through a stereo optical adapter capable of forming two object images of the same object, is displayed. FIG. 9B shows a screen of the monitor 4 after the operation of activating the object distance calculating function is performed. A spot 910 is displayed as a first sight at the center of the left image 900. FIG. 9C shows a screen of the monitor 4 when the user is operating the operation portion 6 to move the spot 910. During this time, the light amount of the LED 29 is modulated so that the spot average luminance of the spot region based on the spot 910 is within a predetermined range.

Figure 9D:
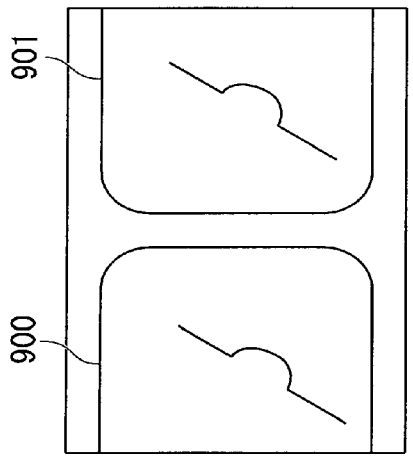
Figure 9E:
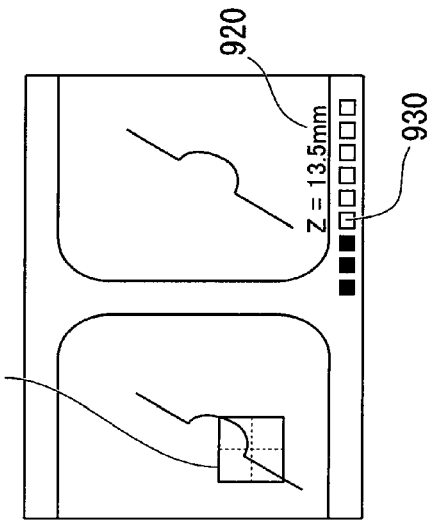

FIG. 9D shows a screen of the monitor 4 after the user stops moving the spot 910. At this time, in the case where the spot average luminance of the spot region based on the spot 910 is within a predetermined range, the object distance calculating process is performed, and the object distance is calculated. FIG. 9E shows a screen of the monitor 4 after the object distance is calculated. A value 920 of the object distance is displayed, and an indicator 930 visually showing the object distance is also displayed.

Figure 7:
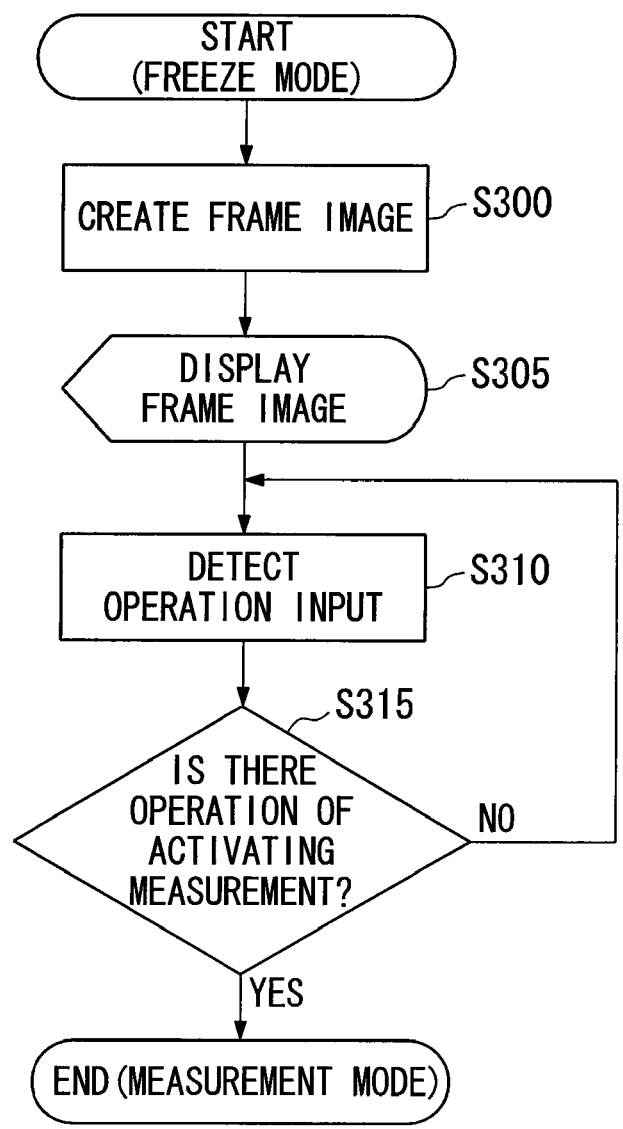
FIG. 7 is a flowchart showing a sequence of an operation of the endoscope apparatus according to the embodiment of the present invention.

As shown in FIG. 7, in the freeze mode, the display signal creating section 49 creates a frame image signal by processing the video signal in order to display the freeze image (still image) on the monitor 4, and creates a display signal by combining the frame image signal with the graphic image signal from the graphic image creating section 43 (Step S300). The monitor 4 displays the frame image together with the operation menu and the like on the basis of the display signal (Step S305).

Subsequently, the control section 47 detects a signal from the operation portion 6 (Step S310), and determines whether or not the user performs an operation of activating the measurement function (Step S315). The operation of activating the measurement function is an operation of inputting an instruction for activating the measurement function. In the case where the user does not perform the operation of activating the measurement, the process returns to Step S310. In addition, in the case where the user performs the operation of activating the measurement, the endoscope apparatus 1 is in a measurement mode.

Figure 8:
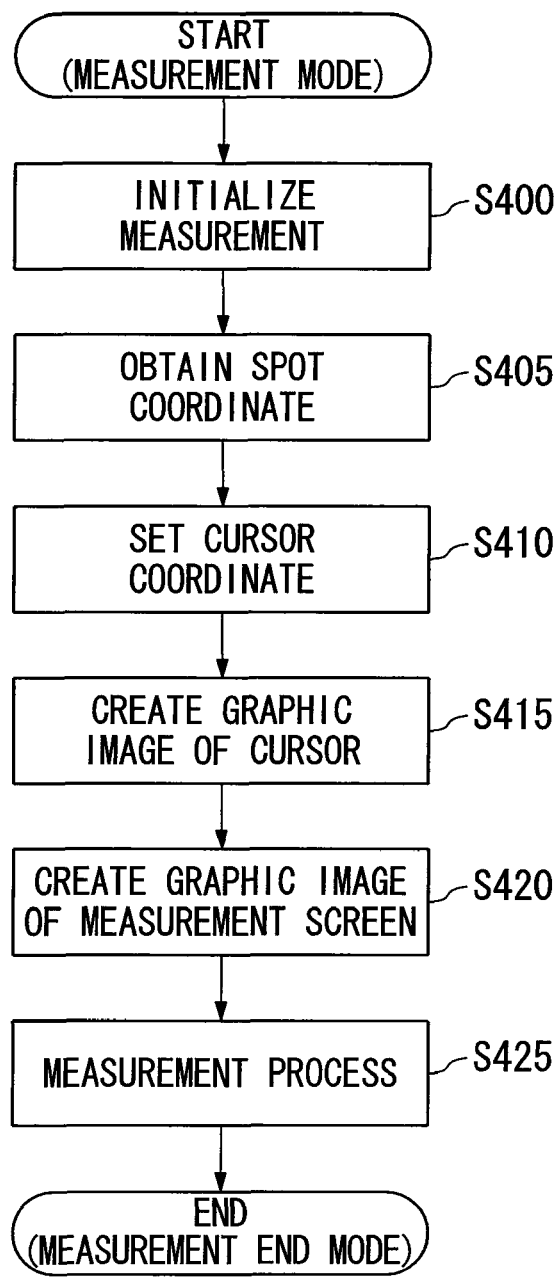
FIG. 8 is a flowchart showing a sequence of an operation of the endoscope apparatus according to the embodiment of the present invention.

As shown in FIG. 8, in the measurement mode, first, a region for various variables is allocated in the RAM 14, and the variables are initialized (Step S400). Subsequently, the operation detecting section 42 calculates the spot coordinate in accordance with the operation of the operation portion 6 operated by the user (Step S405), and stores a cursor coordinate in accordance with the spot coordinate in the RAM 14 (Step S410). At this time, the cursor coordinate identical to the spot coordinate is set.

Subsequently, the graphic image creating section 43 reads the cursor coordinate from the RAM 14, and creates a graphic image signal for displaying a cursor at the position of the cursor coordinate (Step S415). In addition, the graphic image creating section 43 creates a graphic image signal for displaying the measurement screen including the menu and the like required for the measurement (Step S420).

In this way, the activation of the measurement function is completed. The graphic image signal created in Step S415 and Step S420 is output to the display signal creating section 49, and the display signal is created by the display signal creating section 49. The monitor 4 displays an image on the basis of the display signal.

Figure 9F:
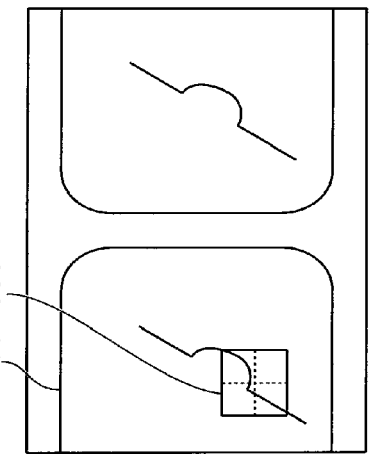

FIG. 9F shows a screen of the monitor 4 after the activation of the measurement function is completed. A cursor 940 as a second sight, an icon 950 such as a menu, and a message 960 for instructing an operation are displayed. FIG. 9F shows a state where the measurement function is activated from the state of FIG. 9E, and the cursor 940 is displayed at a position within a region where the spot region based on the spot 910 was located. In the embodiment, the cursor 940 and the spot 910 are displayed at the same position.

When the activation of the measurement function is completed, the measurement processing section 44 obtains the frame image signal created in Step S300, and performs the measurement process on the basis of the frame image signal (Step S425). The measurement process includes a process of setting a measurement point on the endoscope image on the basis of the operation of the operation portion 6 operated by the user, a process of calculating the area or length designated at the measurement point, and the like. It is preferable that the measurement point be set on the endoscope image at a position where the modulation of the light amount has been performed. That is, the position of setting the measurement point is preferably in the vicinity of the spot coordinate before activating the measurement function, that is, the spot coordinate when the modulation of the light amount was lastly performed. Particularly, the position of setting the measurement point is preferably the same position as the spot coordinate immediately before activating the measurement function.

In the processes shown in FIG. 8, the spot coordinate is continuously monitored and the light amount of the LED 29 is continuously modulated during a period in time from the input of the operation of activating a measurement until the completion of Step S425.

In the above description, one spot region is provided, but plural spot regions may be provided.

For example, the embodiment may be modified and applied to an object distance calculating method using three sights as disclosed in Japanese Unexamined Patent Application, First Publication No. 2006-136706. In this case, for example, three spot regions are respectively set based on the three sights on the endoscope image, the spot average luminance is calculated for each of the spot regions, and the same processes as those of the embodiment may be performed by using the maximum value of the spot average luminance for three spot regions instead of the spot average luminance of FIGS. 5 and 6.

Figure 10:
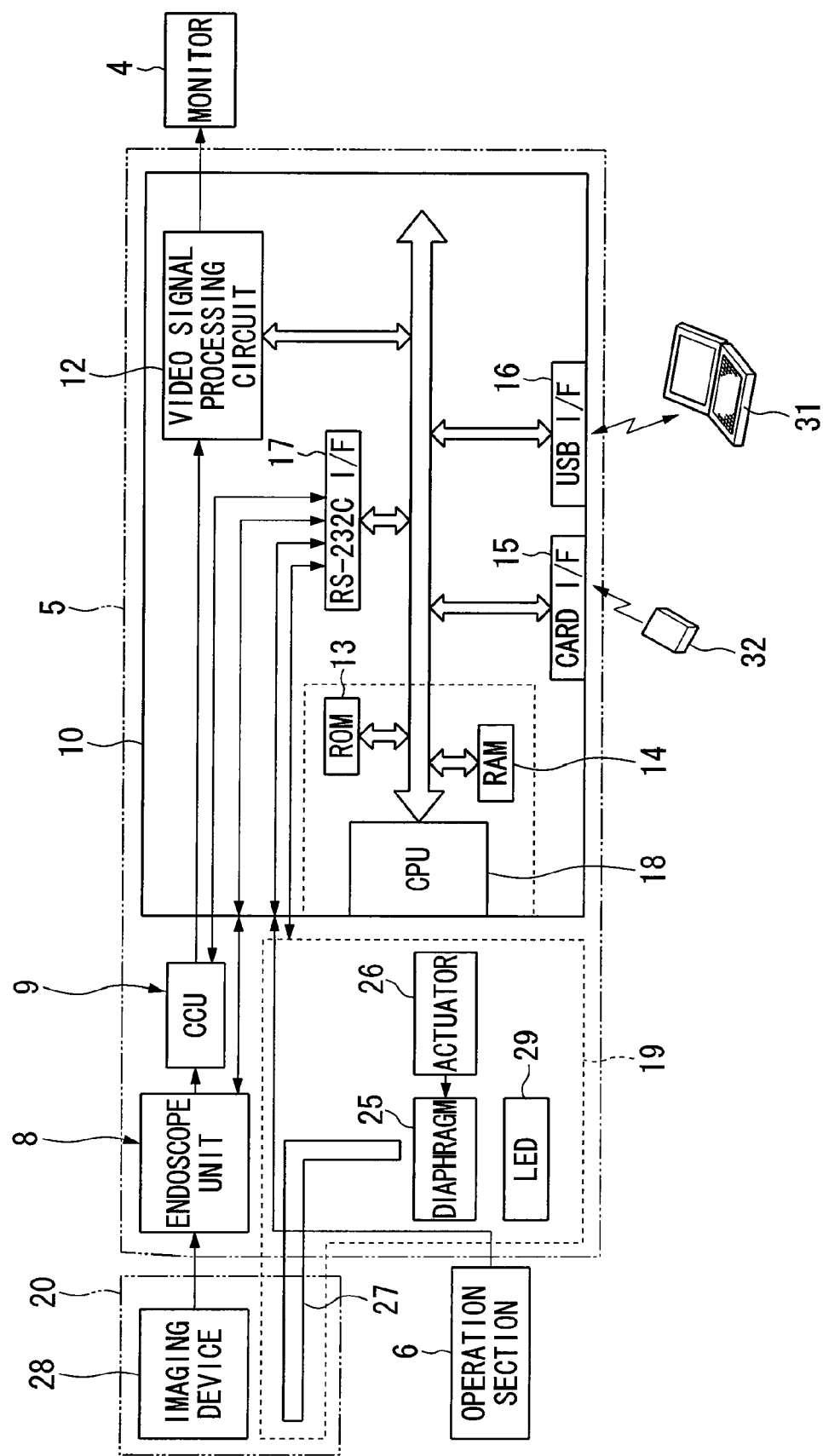
FIG. 10 is a block diagram showing an internal configuration of an endoscope apparatus according to a modified example of the embodiment of the present invention.

In the embodiment, the LED 29 is built in the distal end portion 21, but the LED 29 may be disposed inside the casing 5 so that the illumination light generated by the LED 29 enters the distal end portion 21 through an optical fiber. FIG. 10 shows a configuration in the case where the LED 29 is disposed inside the casing 5. An illuminator 19 is provided with a diaphragm 25 which regulates light emitted from the LED 29, an actuator 26 which drives the diaphragm 25, and a fiber 27 which transmits the regulated light to the distal end portion 21 of the insertion portion 20. The light amount control section 46 drives the actuator 26 on the basis of the luminance detected by the luminance detecting section 45, and modulates the emitted light by using the diaphragm 25. In the embodiment, the LED is used as the illumination, but illumination other than the LED may be used.

As described above, according to the embodiment, the light amount of the LED 29 is modulated on the basis of the luminance of the spot region based on the spot coordinate which is the display position of the spot. As a result, it is possible to perform the measurement by using an image in which the luminance of a region to be measured is appropriately modulated. Accordingly, it is possible to suppress deterioration in the measurement accuracy.

In addition, as shown in FIGS. 5 and 6, the light amount of the LED 29 is modulated in the case where a changing amount of the spot coordinate satisfies a predetermined condition (in the embodiment, the case where the spot coordinate is not changed). As a result, the user is able to determine the timing of modulating the light amount in view of the movement of the spot. Particularly, since the light amount of the LED 29 is controlled in the case where the spot coordinates detected at different time points are identical, that is, the spot coordinate is not changed (or the case where the movement instruction of the spot is not detected), it is possible to perform the modulation of the light amount when the spot is stopped. In addition, since the light amount of the LED 29 is controlled when the spot is stopped, it is possible to improve the measurement accuracy in the case where the measurement point is set to a position which is identical to or in the vicinity of the position where the spot is stopped.

In the embodiment, although the light amount of the LED 29 is controlled in the case where the spot coordinate is not changed, the light amount of the LED 29 may be controlled in the case where the movement speed of the spot coordinate is equal to or less than a predetermined amount, or the light amount of the LED 29 may be controlled in conjunction with the movement of the spot coordinate. In the case where the light amount of the LED 29 is controlled in conjunction with the movement of the spot coordinate, the light amount of the LED 29 may be controlled when the change of the spot coordinate or the instruction of moving the spot is detected. As a result, it is possible to continuously modulate the image so that the luminance is suitable for the measurement, and it is possible to improve the measurement accuracy.

By setting the measurement point to a position based on the spot coordinate and performing the measurement process, it is possible to perform the measurement using the modulated image having the luminance suitable for the measurement, and thus to improve the measurement accuracy. In the embodiment, since the spot position immediately before activating the measurement function is identical to the cursor position immediately after completing the activation of the measurement function, when the measurement point is set in the vicinity of this position (for example, inside of the spot region) and the measurement process is performed, the measurement accuracy is improved. In addition, by setting the measurement point at the spot coordinate and measuring the object distance, it is possible to measure the object distance by using the modulated image having the luminance suitable for the object distance calculation, and thus to improve the accuracy of the object distance calculation.

Note that in the above embodiments, the light amount of the LED is controlled at the time of the stereo measurement using the stereo optical adaptor having two observation fields of view. However, the present invention is not limited to this, and the above-described control of the light amount may be applied to a measurement using an optical adaptor having one observation field of view. Further, the above-described control of the light amount may be applied to any processing, such as observation of the subject, which requires an appropriate control of the light amount at a desired position of the subject.

Figure 12A:
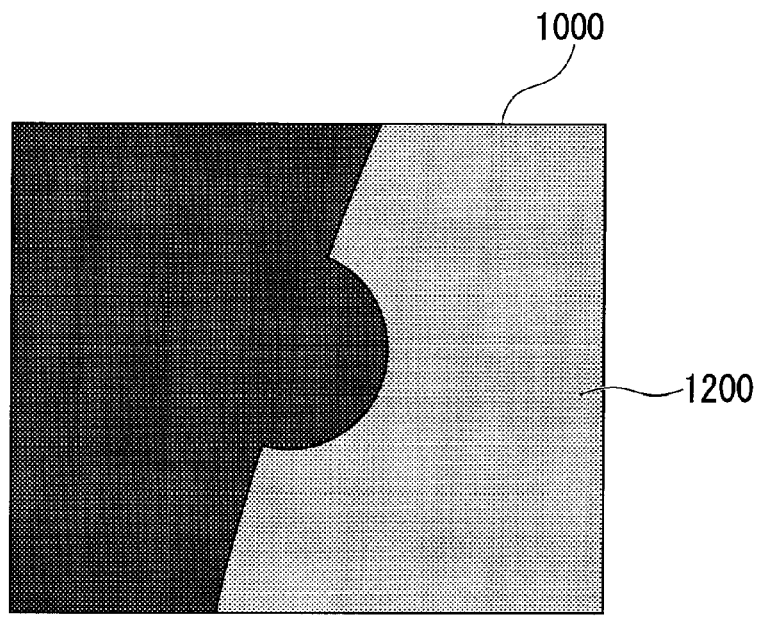
FIGS. 12A and 12B are reference diagrams showing screens according to a modified example of the present invention.
Figure 12B:
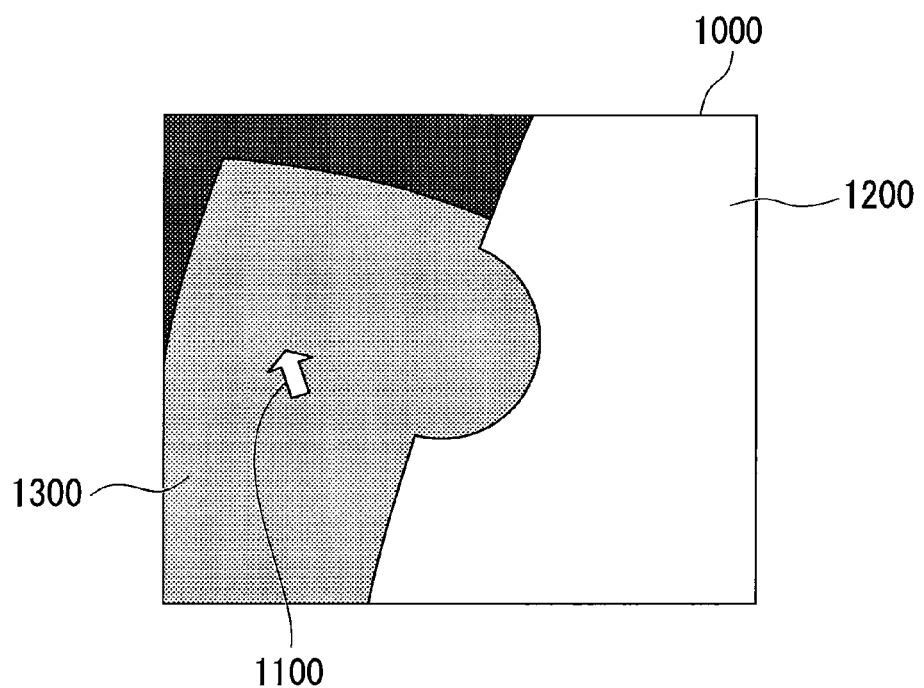

Hereinafter, a modified example of the present invention will be described with reference to FIGS. 12A and 12B. In the present modified example, an operation of the endoscope apparatus 1 when the subject is observed through an optical adaptor having one observation field of view will be described. FIG. 12A shows a screen of the monitor 4 in the live mode. In the present modified example, an image 1000 of the subject imaged through the optical adaptor having one observation field of view is displayed on the monitor 4. When the user performs an operation of activating a modulation of the light amount of the spot, as shown in FIG. 12B, a cursor 1100 as a sight is displayed on the screen of the monitor 4. The control section 47 continuously monitors the display position (i.e., the spot coordinate) of the cursor 1100, and the luminance detecting section 45 calculates an average luminance of a spot region centered on the spot coordinate. Based on the calculated average luminance, the control section 47 continuously controls the light amount of the LED 29 by using the light amount control section 46 and the LED driving section 48. In the present modified example, the monitor of the display position of the cursor 1100 and the control of the light amount of the LED 29 are continuously performed during a period in time from the user's instruction of activating a modulation of the light amount of the spot until the user's instruction of terminating the modulation.

According to the present modified example, it is possible to observe a desired position on the image 1000 of the subject in a state where the luminance condition at the desired position is suitably modulated. In the example shown in FIGS. 12A and 12B, when the user performs an operation of activating the modulation of the light amount of the spot, as shown in FIG. 12B, the light amount of the LED 29 is increased so that the luminance of a partial region based on the cursor 1100 is within a predetermined range. As a result, it becomes possible to observe a blade 1300 located behind a blade 1200, even though the blade 1300 was invisible in the live mode shown in FIG. 12A.

While preferred embodiments of the present invention have been described and illustrated above, it should be understood that these are exemplary of the present invention and are not to be considered as limiting. Additions, omissions, substitutions, and other modifications can be made without departing from the spirit or scope of the present invention. Accordingly, the present invention is not to be considered as being limited by the foregoing description, and is only limited by the scope of the appended claims.

According to the present invention, since the light amount of the illumination is controlled on the basis of the luminance of a partial region based on the display position of the sight on the image, it is possible to perform the measurement by using the image in which the luminance of a region to be measured is suitably modulated, and thus to suppress deterioration in the measurement accuracy.

What is claimed is:

1. An endoscope apparatus comprising:
    an imaging device which takes an image of an object;
    a display which displays the image and a cursor;
    a light source which illuminates the object;
    a pointing device which controls placement of the cursor on the display;
    a memory which stores a spot coordinate corresponding to a position of the cursor on the display; and
    a controller which continuously monitors a cursor position at which the cursor is placed by the pointing device, and changes a luminance of the light source based on a luminance of a spot region of the image so as to modulate a luminance condition of the image, wherein the spot region is a partial region of the image and is centered based on the spot coordinate.

2. The endoscope apparatus according to claim 1, wherein the controller detects the luminance of the spot region of the image, and when the luminance of the spot region of the image is larger than a predetermined value, the controller decreases the luminance of the light source so as to decrease the luminance of the spot region of the image.

3. The endoscope apparatus according to claim 1, wherein the controller detects the luminance of the spot region of the image, and when the luminance of the spot region of the image is smaller than a predetermined value, the controller increases the luminance of the light source so as to increase the luminance of the spot region of the image.

4. The endoscope apparatus according to claim 1, wherein the controller detects the luminance of the spot region to modulate the luminance condition of the image whenever the cursor position is changed by the pointing device.

5. The endoscope apparatus according to claim 1, wherein the controller detects the luminance of the spot region to modulate the luminance condition of the image when there is no input of changing the cursor position by the pointing device.

6. The endoscope apparatus according to claim 1, wherein the controller measures the object by using the cursor under the modulated luminance condition.

7. The endoscope apparatus according to claim 6, wherein when the changing of the luminance of the light source by the controller is completed, the measurement unit calculates an object distance to the object.

8. The endoscope apparatus according to claim 6, wherein the controller measures the object at a measurement position based on the cursor position.

9. The endoscope apparatus according to claim 6, wherein the cursor includes a first cursor and a second cursor, the controller changes the luminance of the light source in accordance with the luminance of the spot region of the image, which is centered based on a spot coordinate corresponding to a first cursor position, and the controller measures the object by using a second cursor position as the measurement position.

10. The endoscope apparatus according to claim 9, wherein an initial second cursor position is within the spot region of the image at the time when the controller changes the luminance of the light source in accordance with the luminance of the spot region of the image.

11. The endoscope apparatus according to claim 9, wherein an initial second cursor position is identical to the first cursor position at the time when the controller changes the luminance of the light source in accordance with the luminance of the spot region of the image.

12. The endoscope apparatus according to claim 1, wherein the display further displays a menu, and when the pointing device places the cursor within the menu, the cursor functions as a menu operation cursor.

13. A method for an endoscope apparatus comprising a display, a pointing device, and a controller, the method comprising:
    acquiring an image of an object;
    displaying, on the display, the image of the object and a cursor on a display of an endoscope apparatus;
    continuously acquiring a spot coordinate corresponding to a cursor position on the display, the cursor position being a position at which the cursor is placed on the display by the pointed device; and
    modulating a luminance condition of the image by changing a luminance of a light source of the endoscope apparatus based on a luminance of a spot region of the image, wherein the spot region is a partial region of the image and is centered based on the spot coordinate.

14. The method according to claim 13, wherein the modulating the luminance condition of the image includes decreasing the luminance of the light source so as to decrease the luminance of the spot region of the image when the luminance of the spot region of the image is larger than a predetermined value.

15. The method according to claim 13, wherein the modulating the luminance condition of the image includes increasing the luminance of the light source so as to increase the luminance of the spot region of the image when the luminance of the spot region of the image is smaller than a predetermined value.

16. The method according to claim 13, wherein the modulating the luminance condition of the image is repeated whenever the cursor position is changed.

17. The method according to claim 13, wherein, in the modulating the luminance condition of the image, the luminance of the light source is controlled substantially in real time with a movement of the cursor.

18. The method according to claim 13, wherein, in the modulating the luminance condition of the image, the luminance of the light source is changed only when the cursor is stopped.

19. The method according to claim 13, further comprising a calculating an object distance to the object under the luminance condition having been modulated after the modulating the luminance condition of the image is performed.

20. The method according to claim 13, further comprising measuring the object by using the cursor under the luminance condition having been modulated.

21. The method according to claim 20, wherein, in the measuring the object, the object is measured at a measurement position based on the cursor position on the display.

* * * * *